United States Patent [19]

Fujita et al.

[11] 3,981,889

[45] Sept. 21, 1976

[54] METHOD OF MANUFACTURING CIS,CIS-2,4,6-TRIISOPROPYL-1,3,5-TRIOXANE

[75] Inventors: Masao Fujita, Amagasaki; Takuya Akiyama, Nagaokakyo; Yoshito Saeki, Suita; Yasuhiko Ueno, Kawanishi, all of Japan

[73] Assignee: Ogawa & Co., Ltd., Japan

[22] Filed: Apr. 22, 1974

[21] Appl. No.: 463,175

[30] Foreign Application Priority Data
June 4, 1973 Japan............................. 48-64116
June 4, 1973 Japan............................. 48-64117
Nov. 6, 1973 Japan............................. 48-126043

[52] U.S. Cl. ............................................... 260/340
[51] Int. Cl.² ....................................... C07D 323/04
[58] Field of Search ................................... 260/340

[56] References Cited
FOREIGN PATENTS OR APPLICATIONS
748,430 12/1966 Canada............................ 260/340
319,368 3/1920 Germany........................... 260/340
373,059 12/1963 Switzerland....................... 260/340
1,199,650 12/1974 United Kingdom................. 260/340

OTHER PUBLICATIONS

H. Meyer, Synthese der Kohlenstoffverbindungen, Heterocyclen, Zweiter Teil, 1, Halfte (1940), p. 452.

W. J. Hickinbottom, Reactions of Organic Compounds, (1948), pp. 192–193.

Yoshiki Oshiro et al., Kogyo Kagaku Zasshi, 70, 1329 (1967).

*Primary Examiner*—Norma S. Milestone
*Attorney, Agent, or Firm*—Wenderoth, Lind & Ponack

[57] ABSTRACT

Method of producing cis,cis-2,4,6-triisopropyl-1,3,5-trioxane by cyclic trimerization of isobutylaldehyde in the presence of a strong acid catalyst.

2 Claims, No Drawings

METHOD OF MANUFACTURING CIS, CIS-2, 4, 6-TRIISOPROPYL-1, 3, 5-TRIOXANE

The present invention relates to a method for manufacturing Cis, Cis-2, 4, 6-Triisopropyl-1, 3, 5-trioxane comprising cyclic trimerization of Isobutylaldehyde under the effect of a strong acid with or without mixing a solvent therein. (For convenience sake, Cis, Cis-2, 4, 6-Triisopropyl-1, 3, 5-trioxane will be denoted by C-C hereinunder.)

This conventionally-known crystal composite, characterized as sublimable, nontoxic, odorless, tasteless, unstimulative, and high in melting point (62.5°C), has been little utilized heretofore, despite its various advantageous properties as above-mentioned, as a raw material for producing sublimable chemicals. There had been no established method for producing C—C although an experimental synthesis of said composite has been reported in a chemical magazine in Japan (Kogyo Kagaku Zasshi (Industrial Chemical Magazine) 70, 1329 (1967)). The experiment has proven unsuccessful from a view point of industrial production because of various faults found in reaction operation, reaction-temperature control, post factum disposal and the like involved therein, according to tests conducted on said method by the present inventors.

A main object of the present invention is to provide a method favorable for manufacturing C—C so as to make it really useful among the chemical industrial circles, the method corresponding to a method for cyclically trimerizing Isobutylaldehyde by means of putting it under the effect of strong acid as a catalyzer with or without conducting a preliminary process of dissolving the Isobutylaldehyde with solvent.

In case of using solvent, any solvent, except one being obstructive to the cyclic-trimerization, is admissible but the following are preferable from an industrial view point: aliphatic hydrocarbon such as n-hexane, n-pentane, and the like; aromatic hydrocarbon such as benzene, toluene and the like; halogenated hydrocarbon such as methylene chloride, ethylene dichloride and the like; ether such as diethyl ether, anisole and the like; and ester such as ethyl acetate, ethyl propionate and the like.

The amount of solvent is required not to be so large as to hinder the reaction operation. It is acceptable that the amount of solvent be as much as the Isobutylaldehyde in weight. Reaction temperature is to range from −20° to 70°C but preferably from 0° to 50°C. (Hereinunder, description of mol ratio between catalyzers and Isobutylaldehyde will be based on 1 mol of the latter.)

Preferable strong acids to apply as a catalyzer to the method in the present invention are: (1) Brønsted acid group: sulfuric acid, phosphoric acid, hydrogen halide, fuming nitric acid, benzene sulfonic acid, toluene sulfonic acid, strong cation acid exchange resin, and the like each having the least content of water, each of their mixing ratio to Isobutylaldehyde being more than 0.0001 mol, preferably 0.0004 − 0.04 mol; (2) Lewis acid group: aluminum chloride, zinc chloride, boron trihalide, phosphorous trihalide and the like, each of their mixing ratio to Isobutylaldehyde being more than 0.0001 mol, preferably 0.0004 − 0.04 mol.

Either batch system or continuous system can be applicable to the reaction.

Unrefined composite produced in the above-said process is dealt with by a conventionally-known method thereby obtaining refined C—C therefrom.

Following examples serve to illustrate the preferred method for preparing C—C, without imposing any limitation on the present invention.

EXAMPLE 1:

Into a hard-glass-made, four-necked flask of 10 liter capacity equipped with a refluxed condenser, a thermometer, a funnel and a stirrer, was put 3.6 kg of Isobutylaldehyde (50 mol) and another 3.6 kg of benzene, the mixture being kept at 3°C Then there was added thereto, while strongly stirring the mixture, 18.4 g (0.184 mol) of 98% sulfuric acid all at once, the mixture thence soaring to 42°C 2 minutes later. The mixture was cooled under stirring until the reaction terminates four hours later. Organic layer thereof was washed once with 500 cc water and thence twice with 500 cc of aqueous solution of sodium bicarbonate, and then dried with anhydrous magnesium sulphate.

By way of filtering the anhydrous magnesium sulphate, both unreacted Isobutylaldehyde and benzene were recovered thereby gaining a crude product of 3.42 kg therefrom. The crude product was recrystalized from an equivalent weight amount of methanol thereby obtaining 3.24 kg of pure Cis, Cis-2, 4, 6-Triisopropyl-1, 3, 5-trioxane (melting point 62.5°C), the yield being 90%.

EXAMPLE 2:

Into the flask as described in the above example was put 3.6 kg of Isobutylaldehyde (50 mol) and another 3.6 kg of benzene, adding thereto under cooling 102 g of anhydrous zinc chloride (0.75 mol) all at once, thereby cyclically trimerizing the Isobutylaldehyde to produce 3.17 kg of Cis, Cis-2, 4, 6-Triisopropyl-1, 3, 5-trioxane in a state of pure crystal. The yield was 88% in this case.

In case of using sulfuric acid and phosphoric acid as a catalyst, no solvent is necessary for the reaction and, instead, these chemicals have to be controlled in weight percentage. Unless the percentages are limited, there will be, at the time of completion of the reaction, generation of the isomer Cis, Trans-2, 4, 6-Triisopropyl-1, 3, 5-trioxane (denoted by C—T hereinunder) which is inferior to C—C in quality, the melting point of C—T being 39.5° − 40°C compared to 62.5°C for C—C.

EXAMPLE 3:

Into a 300 ml flask identical with that used in the above examples was put 80-weight % phosphoric acid, 200 g (1.63 mol) in quantity. Under cooling to 3° − 5°C and under strong stirring, there was added thereto 72 g of Isobutylaldehyde (1 mol) dropwise, taking one hour to complete the addition, and the mixture, at the same temperature, was stirred continuously for an additional one hour. After completion of the reaction process, 150 ml of n-hexane was mixed therein, thereby separating the layer of n-hexane therefrom. The mixture was then washed once with 50 ml saturated salt water and twice with 50 ml of aqueous solution of sodium bicarbonate, and then dried with anhydrous magnesium sulphate. By way of filtering out the anhydrous magnesium sulphate and recovering the n-hexane therefrom, 69 g of crude product was obtained. The crude product yielded 61 g pure C-C (melting point 62.5°C), recording 85% yield.

Phosphoric acid in weight percentage ranging from 75% to 85% is best effective for this reaction process, i.e. observing no generation of the C–T isomer. When it was 70%, for example, there was a byproduct of C–T at a rate of 8% contained in the C—C, and the yield of C—C was only 52%. When the weight percentage was 90%, on the other hand, there was also a byproduct of high boiling-point material, the yield of C—C recording 64%. The mol ratio of phosphoric acid to Isobutylaldehyde is selected from between 0.1 and 10 but preferably, for the sake of reaction operation, between 0.5 and 3. Reaction temperature is −20° ~ 40°C but preferably −5° ~ 10°C. Recovered phosphoric acid can be used for the next reaction.

EXAMPLE 4:

Into a flask identical with that described in the above Example 3 was poured 55-weight % sulfuric acid, 200 g (1.13 mol) in quantity, keeping this material at 3°C − 5°C. Under strong stirring there was added thereto 72 g (1 mol) of Isobutylaldehyde dropwise, the addition taking one hour to complete. The reaction was completed after stirring the mixture at the same temperature for an additional 1 hour.

N-hexane, 150 ml in quantity, was mixed with the reaction-completed composite, and after separating the layer of the n-hexane therefrom, the composite was washed once with 50 ml saturated salt water and twice with 5% aqueous solution of sodium bicarbonate, 50 ml in quantity each, and dried with anhydrous magnesium sulphate. By way of filtering out the anhydrous magnesium sulphate and recovering the n-hexane therefrom, there was obtained 59 g of crude product. The crude product was recrystalized from an equivalent weight amount of methanol, thereby producing pure C-C (melting point 62.5°C) of 54 g in weight. The yield was 75%.

Sulfuric acid is best available for this purpose in weight percentage ranging from 52% to 60%. When it was 45%, for example, there was 14% C—T produced and the yield of C—C was only 25%, with the cyclic-trimerizing rate being 52%. On the other hand, when the weight percentage of sulfuric acid was 65%, a high-boiling-point material was by-produced, and the yield of C—C was 33%.

Mol rate of sulfuric acid to Isobutylaldehyde can also be selected from between 0.1 and 10, but preferably between 0.5 and 3 for the sake of reaction operation. Reaction temperature is −20° to 40°C but preferably −5° to 10°C.

What is claimed is:

1. A method for producing cis,cis-2, 4, 6-triisopropyl-1, 3, 5-trioxane by cyclic trimerization of isobutylaldehyde, which comprises adding dropwise under stirring isobutylaldehyde to a 52 to 60 weight % solution of sulfuric acid, and stirring the resultant mixture after the addition is completed, the reaction temperature being from −5°C to 10°C and the mole ratio of sulfuric acid to isobutylaldehyde being from 0.1:1 to 10:1.

2. A method for producing cis,cis-2, 4, 6-triisopropyl-1, 3, 5-trioxane by cyclic trimerization of isobutylaldehyde, which comprises adding dropwise under stirring isobutylaldehyde to a 75 to 85 weight % solution of phosphoric acid, and stirring the resultant mixture after the addition is completed, the reaction temperature being from −5°C to 10°C and the mole ratio of phosphoric acid to isobutylaldehyde being from 0.1:1 to 10:1.

* * * * *